(12) United States Patent
Yukon

(10) Patent No.: US 7,901,574 B2
(45) Date of Patent: Mar. 8, 2011

(54) QUICK DISCONNECT LIQUID CHROMATOGRAPH COLUMNS

(75) Inventor: E. Daniel Yukon, Stoughton, MA (US)

(73) Assignee: E. Daniel Yukon, Stoughton, MA (US)

( * ) Notice: Subject to any disclaimer, the term of this patent is extended or adjusted under 35 U.S.C. 154(b) by 115 days.

(21) Appl. No.: 12/364,324

(22) Filed: Feb. 2, 2009

(65) Prior Publication Data

US 2010/0193439 A1 Aug. 5, 2010

(51) Int. Cl.
*B01D 15/08* (2006.01)

(52) U.S. Cl. .............. 210/198.2; 210/232; 210/656; 96/101; 285/33; 285/39; 285/388

(58) Field of Classification Search ............ 210/198.2, 210/656, 232; 96/101, 106; 285/33, 39, 285/388
See application file for complete search history.

(56) References Cited

U.S. PATENT DOCUMENTS

| | | | | |
|---|---|---|---|---|
| 944,877 A * | 12/1909 | Koschinski | .............. | 285/388 |
| 1,726,683 A * | 9/1929 | Schramm | .............. | 439/809 |
| 1,977,179 A * | 10/1934 | Fisch | .............. | 439/761 |
| 2,225,654 A * | 12/1940 | Olson | .............. | 411/176 |
| 3,487,938 A * | 1/1970 | Patterson | .............. | 210/198.2 |
| 3,488,073 A * | 1/1970 | Wold | .............. | 285/388 |
| 4,313,828 A | 2/1982 | Brownlee | | |
| 4,343,496 A * | 8/1982 | Petranto | .............. | 285/39 |
| 4,451,364 A | 5/1984 | Higgins et al. | | |
| 4,451,365 A | 5/1984 | Sattler et al. | | |
| 4,586,733 A | 5/1986 | Anderson, Jr. | | |
| 4,737,284 A * | 4/1988 | Hauke et al. | .............. | 210/198.2 |
| 4,806,238 A * | 2/1989 | Sattler et al. | .............. | 210/198.2 |
| 4,865,728 A * | 9/1989 | Larsson | .............. | 210/198.2 |
| 4,876,005 A | 10/1989 | America | | |
| 4,968,421 A | 11/1990 | Spacek et al. | | |
| 5,167,810 A * | 12/1992 | Vassarotti et al. | .............. | 210/198.2 |
| 5,194,225 A * | 3/1993 | Muller et al. | .............. | 422/70 |
| 5,299,842 A | 4/1994 | Marks et al. | | |
| 5,366,621 A | 11/1994 | Bidell et al. | | |
| 5,378,361 A * | 1/1995 | Baeckstrum | .............. | 210/198.2 |
| 5,601,708 A * | 2/1997 | Leavesley | .............. | 210/198.2 |
| 6,090,190 A * | 7/2000 | Enhsen et al. | .............. | 96/101 |
| 6,171,486 B1 | 1/2001 | Green et al. | | |
| 6,932,904 B2 * | 8/2005 | Laub et al. | .............. | 210/198.2 |
| 7,364,655 B2 | 4/2008 | Demarco | | |
| 2007/0090035 A1 | 4/2007 | Rahn et al. | | |
| 2007/0170110 A1 * | 7/2007 | Onoue et al. | .............. | 210/444 |
| 2008/0230454 A1 * | 9/2008 | Nibler et al. | .............. | 210/167.12 |

FOREIGN PATENT DOCUMENTS

| | | |
|---|---|---|
| EP | 0 476 995 A2 | 9/1991 |
| EP | 1 306 668 A1 | 10/2002 |
| JP | 2007-71730 A | 3/2007 |

OTHER PUBLICATIONS

Machine language translation of Japan Patent No. 2007-071730.*

* cited by examiner

*Primary Examiner* — Ernest G Therkorn
(74) *Attorney, Agent, or Firm* — Sampson & Associates, P.C.

(57) ABSTRACT

A chromatography column comprising a chromatography tube, a piston tube with a porous obstruction that inhibits the movement of particle solids therethrough, and a quick connect/disconnect clamp for use in coupling the chromatography tube to the piston tube. This column is for use in a liquid chromatography process where fluid is pumped under pressure through the chromatography tube which contains a packed particulate solid. The clamp allows for the quick removal and replacement of chromatography tubes when the particulate needs replacement.

14 Claims, 6 Drawing Sheets

QUICK DISCONNECT LIQUID CHROMATOGRAPH COLUMNS

TECHNICAL FIELD

This invention relates to liquid chromatography and more particularly to liquid chromatography columns.

BACKGROUND INFORMATION

Chromatography (from Greek χρῶμα:chroma, color and γραφειν:graphein to write) is the collective term for a family of laboratory techniques for the separation of mixtures. It involves passing a mixture dissolved in a "mobile phase" through a "stationary phase", which separates the analyte to be measured from other molecules in the mixture and allows it to be isolated.

Liquid chromatography is one subset of chromatography processes used for chemical separation. A liquid eluent/mobile phase is passed through an adsorbent/stationary phase. This stationary phase, in many systems, is contained in a chromatography column.

In 1978 W. C. Still introduced an improved form of column chromatography called flash column chromatography where the eluent or mobile phase is pushed through the column, containing the stationary phase, under a positive pressure. This pressure can be substantial.

Before being used, a chromatography tube must typically first be packed with the stationary phase such that it is evenly distributed to achieve the best possible separation in the chromatography process. This may be accomplished in various ways but it is desirable for the result to be a fully packed chromatography tube with evenly distributed stationary phase particles which typically vary in size within a given manufactured range.

Interchangeable chromatography columns which can be attached in line with a chromatography process come in a variety of different configurations. It is important that these columns can be efficiently connected and disconnected to the chromatography system. One of the practical problems with these existing configurations is that disconnecting them in liquid chromatography systems can be physically difficult for technicians due to residual pressure in the system. Physical acts such as pushing against pressure and turning, or unscrewing a pressure loaded connection may place a technician in a position where they undergo harmful repetitive motion in their work or have to rely on third parties to perform their work.

SUMMARY

In accordance with one aspect of the invention, a chromatography column includes a chromatography tube with an opening at both ends, and a piston tube with an opening at both ends. This piston tube has an outer diameter smaller than the inner diameter the chromatography tube. The piston tube also has at least one porous layer obstructing a transverse cross section of its interior. The chromatography tube and piston tube are held in fluid communication with each other by at least one chromatography clamp that may be opened or closed. In the closed position the clamp extends around substantially 360 degrees of the periphery of the chromatography tube, but no one component of the chromatography clamp extends around substantially 360 degrees of the chromatography tube.

In another aspect, a method for connecting a chromatography tube to a liquid chromatography process is described. This method includes providing a chromatography clamp that can be opened or closed and when closed extends substantially 360 degrees around the periphery of a chromatography tube, but no one component of the chromatography clamp encircles substantially 360 degrees of said chromatography tube. A piston tube is provided which is open at both ends and has a smaller exterior diameter than the interior diameter of the aforementioned chromatography tube. The piston tube further has at least one porous layer obstructing a transverse cross section of the tube's interior. The clamp is opened, and then closed and fastened around the chromatography tube and piston tube coupling them and holding them in fluid communication with each other.

In a still further aspect of the invention a chromatography column for use in a liquid chromatography process is configured to connect to an overall chromatography system which then conveys eluent through the column and through the adsorbent contained in the column. This column is comprised of a chromatography tube with an opening at both ends. At least one of the openings is flanged. There is also a piston tube with an opening at both ends and an outer diameter smaller than the inner diameter of the chromatography tube. The outer surface of this piston tube is threaded and has at least one porous layer obstructing a transverse cross section of its interior. A collar for the piston tube is threaded on the interior surface to threadably engage the piston tube.

This collar captures the piston tube by rotating the collar and piston tube relative to each other so that the exterior threads of the piston tube are captured by the interior threads of the collar.

The chromatography column also includes at least one chromatography clamp, configured to open along a substantially axial plane. The clamp is configured to capture the flange on the chromatography tube and the collar (which has been threaded onto the piston tube) thereby holding the chromatography tube and piston tube in axial alignment. The chromatography clamp is free to rotate relative to the chromatography tube and piston tube. The piston tube and chromatography tube are not free to rotate relative to each other. Consequently turning the clamp around the chromatography tube turns the internally threaded collar around the piston tube forcing the piston tube to move axially in or out of the chromatography tube.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

BRIEF DESCRIPTION OF THE DRAWINGS

The above and other features and advantages of this invention will be more readily apparent from a reading of the following detailed description of various aspects of the invention taken in conjunction with the accompanying drawings, in which.

DETAILED DESCRIPTION

Figure 1:
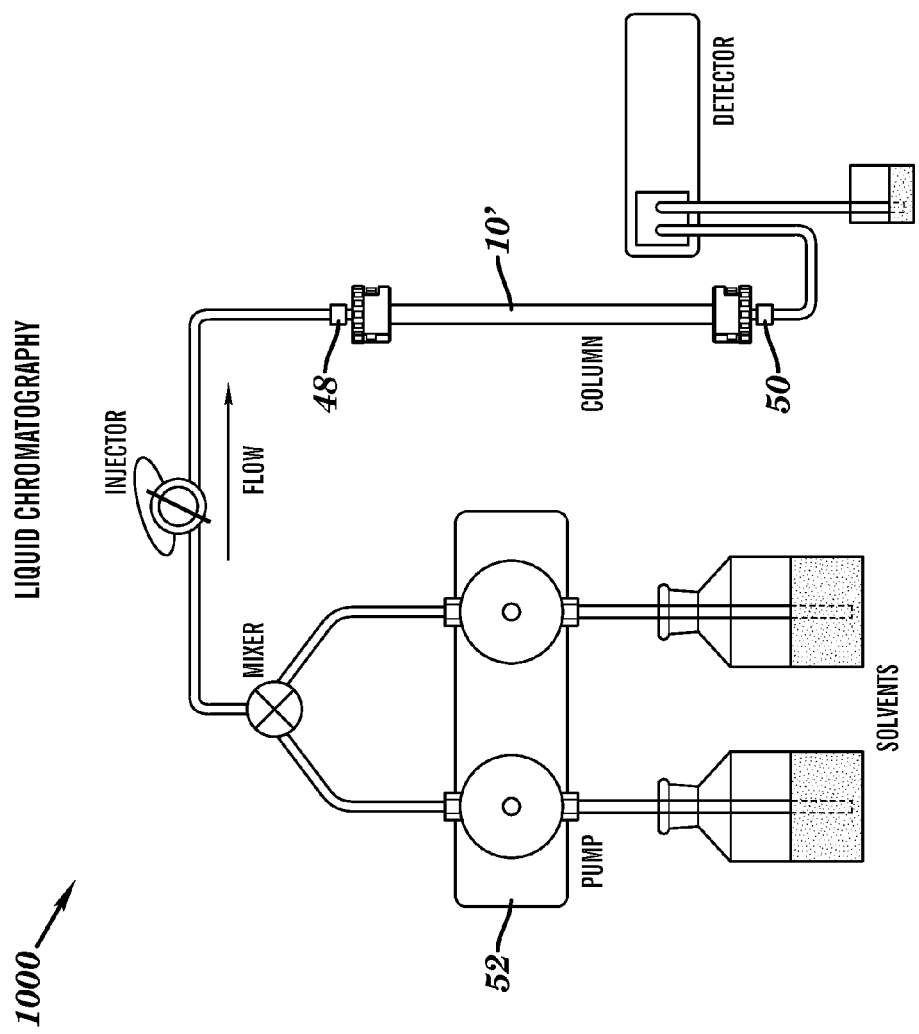
FIG. 1 is a schematic view of an embodiment of the present invention incorporated into a chromatography process.

Applicant has devised a new chromatography column that allows for the exchange of chromatography tubes in a chromatography system. The applicant has configured a column with a quick release chromatography clamp that allows for the technician to easily connect and disconnect the column with a minimal application of force. This allows for easier and faster transfer of chromatography tubes which reduces the burden on technicians and improves system efficiency.

In the following detailed description, reference is made to the accompanying drawings that form a part hereof, and in which is shown by way of illustration, specific embodiments in which the invention may be practiced. These embodiments are described in sufficient detail to enable those skilled in the art to practice the invention, and it is to be understood that other embodiments may be utilized. It is also to be understood that structural, procedural and system changes may be made without departing from the spirit and scope of the present invention. The following detailed description is, therefore, not to be taken in a limiting sense, and the scope of the present invention is defined by the appended claims and their equivalents. For clarity of exposition, like features shown in the accompanying drawings are indicated with like reference numerals and similar features as shown in alternate embodiments in the drawings are indicated with similar reference numerals.

An embodiment of the subject invention includes a chromatography tube. At each open end of the chromatography tube a chromatography clamp, threaded on its interior surface, is used to capture and hold a piston tube, threaded on its exterior surface, in fluid communication with the aforementioned chromatography tube. The clamp captures a flange on the end of the chromatography tube and the threads of the piston tube, thereby holding the tubes in alignment. The chromatography tube is configured to receive a particulate solid therein. This solid is restrained from passing through the tube by a porous obstruction, such as a screen, which may be located across one end of the piston tube. The piston tube is restrained from rotating, relative to the chromatography tube, by a medium such as a flexible o-ring that fits between the inner piston tube and outer chromatography tube. The closed chromatography clamp is free to rotate around the piston tube and chromatography tube. In doing so the clamp forces the piston tube to move axially relative to the chromatography tube. By turning a chromatography clamp a piston tube may be moved into the chromatography tube until the particulate solid is compacted. Fluid may then be pumped in through one piston tube into the chromatography tube where it interacts with the particulate. Separation occurs, in a conventional manner recognizable to one skilled in the art. The fluid then flows out the opposite piston tube where it is collected.

Once the process has been completed the pumping of the fluid is stopped and the quick release clasp on each clamp may be easily unfastened. The chromatography tube, with the spent particulate solid stationary phase, may then be removed and quickly and easily replaced in order to begin a new process.

Figure 2:
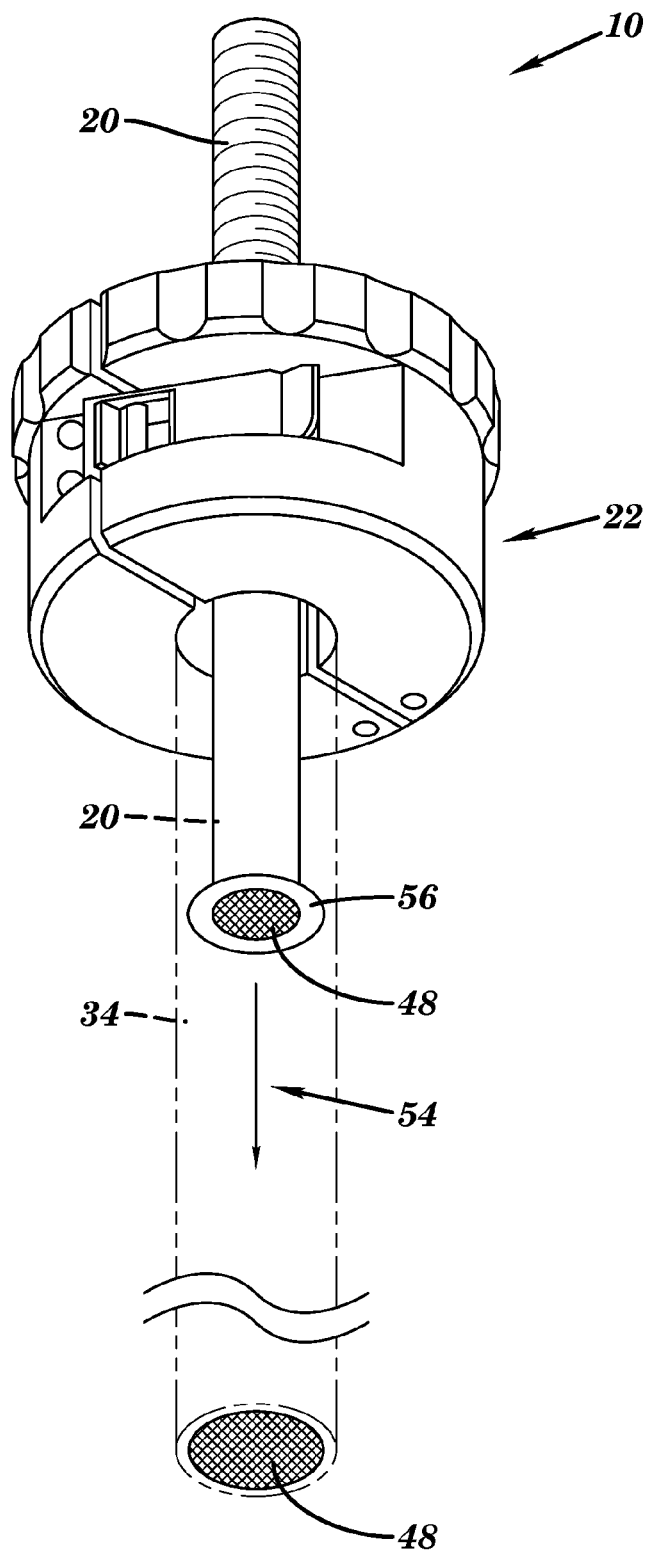
FIG. 2 is a perspective view of an embodiment of the subject invention usable in FIG. 1.

An additional benefit of some embodiments is that the clamp is a single piece held together by some movable connecter such as a hinge. This means relatively few components to keep track of when installing the column. Since the clamping is approached substantially from the sides, rather than axially, manipulating the fastener to open or close the clamp has the additional benefit of requiring the application of substantially less force than conventional approaches such as twisting or turning a threaded connector.

Where used in this disclosure, the term "axial" when used in connection with an element described herein, refers to a direction parallel to the flow path and/or downstream flow of the process solution therethrough (54) (FIG. 2). The term "axial plane" refers to a plane that would include a vector in the axial direction. Similarly, the term "transverse" refers to a direction substantially orthogonal to the axial direction. The term upstream is used to describe the direction from which the process fluid is introduce into the column, likewise downstream is used to describe the direction in which the process fluid would exit the column.

Turning now to the figures, embodiments of the present invention will be discussed in detail. Referring to FIG. 1, an embodiment of the chromatography column (10') is shown incorporated into a typical chromatography process (1000). One piston tube (20) may be connected via a conventional threaded pressure fitting to the upstream connection (48). A second piston tube (20) may be connected via a standard threaded pressure fitting to the downstream connection (50). Each piston tube (20) is connected via a clamp (22) to each end of a chromatography tube (34). A pump (52) then forces fluid under pressure through the upstream piston tube (20), through the chromatography tube (34) which contains a particulate stationary phase. The interaction of the process fluid (or eluent) with the stationary phase (or adsorbent) causes separation of the analyte (the material to be separated) from the fluid solution.

Referring to FIG. 2, in another embodiment, a chromatography column (10) for use in a liquid chromatography process is shown. The column (10) comprises a chromatography tube (34), a chromatography clamp (22), a collar or nut block (26) (FIG. 3), and a piston tube (20) The piston tube (20) has a smaller outer diameter than the inner diameter of the chromatography tube (34). The nut block (26) (FIG. 3) is threadably engaged with the piston tube (20). When the chromatography clamp (22), which in the embodiment shown separates along its axial plane (54) (FIG. 3), is closed and fastened to couple and seal the piston tube (20) to an end of the chromatography tube (34), the nut block 26 (FIG. 3) is held in place and is substantially prevented from moving relative to the chromatography clamp (22). A porous obstruction, such as a screen (48), may be located at the end of the piston tube (20) most interior to the chromatography tube in order to substantially prevent a particulate stationary phase (inserted by a user as discussed in greater detail hereinbelow) from passing between the chromatography tube (34) and the piston tube (20). The piston tube (20) may be prevented from rotating relative to the chromatography tube (34) by the use of an o-ring (56) disposed in a substantially fluid-tight fit between tubes (34) and (20). As shown, it may be desirable to locate the o-ring (56) close to the end of the piston tube (20) having the porous obstruction, to help minimize movement of the stationary phase particles into the space between the piston tube (20) and the chromatography tube (34). The piston tube (20) may also be provided, with an annular groove (not shown) sized and shaped to receive and capture the o-ring (56) at this desired location. The groove may be provided in any convenient manner, such as by machining, molding, etching, etc. The clamp (22) may rotate relative to the chromatography tube (34) and piston tube (20) whereby the clamp

(22) exerts an axial force causing the piston tube (20) to move relative to the chromatography tube (34).

Is should be noted that the end of the chromatography tube opposite the clamp (not shown) may be coupled to the chromatography process in substantially any manner known to those skilled in the art. Such coupling may be configured in various ways to facilitate the chromatography process. For example, a second clamp may be used or a nozzle, filter or other type of obstruction may be provided to prevent the stationary phase from passing out of the chromatography tube (34) while still allowing the process fluid to flow through the tube (34). For example, one such optional approach would be to provide column (10) with a second porous obstruction (48) disposed substantially permanently near the open end of the chromatography tube (34) opposite the clamp (22) as shown in phantom. This may eliminate the need for use of a second clamp (22) at that open end.

Figure 3:
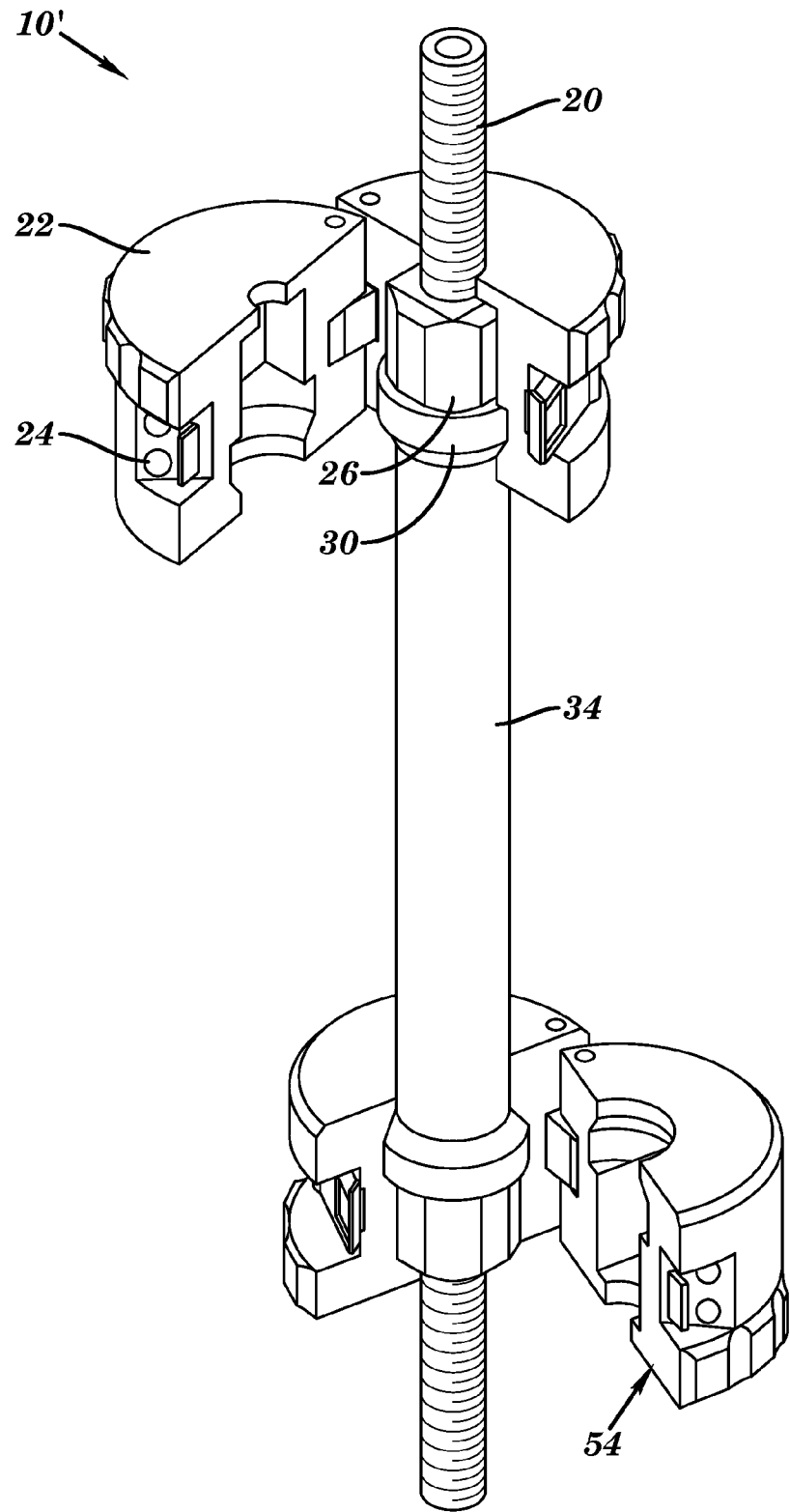
FIG. 3 is a perspective view of an alternate embodiment of the subject invention.

Referring to FIG. 3, in another embodiment, the invention is a chromatography column for use in a liquid chromatography process. The column (10') is substantially similar to column 10, while also including a second chromatography clamp (22), and a second piston tube (20). The two chromatography clamps (22), which separate along their axial plane (54), are closed and fastened to couple and seal one piston tube (20) to each end of chromatography tube (34) holding the tubes in fluid communication with each other. The piston tubes may have a porous obstruction (48) (FIG. 1), such as a screen, located at the end of the piston tubes (20) most interior to the chromatography tube (34). The ends of the piston tubes (20) farthest away from the chromatography tube (34) may be threaded or fitted with some other high pressure connection for attaching the column in line with the chromatography process. The quick release clasps (24) may be easily unfastened allowing the clamps (22) to open and a chromatography tube (34) may be easily removed or connected.

Figure 4:
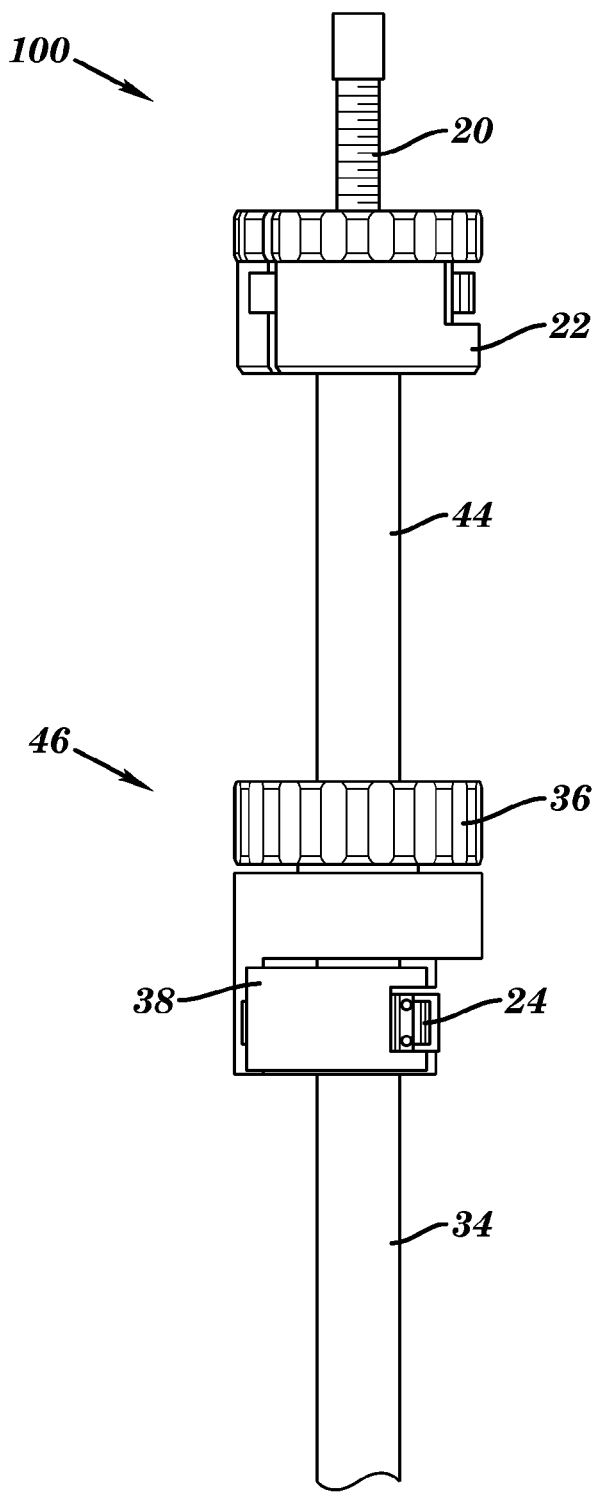
FIG. 4 is a perspective view of an alternate embodiment of the subject invention.

Referring to FIG. 4, in another embodiment shown as tube assembly (100), the chromatography tubes (34) of FIGS. 1 &2 may be filled with slurry made by mixing stationary phase particulate with a fluid. This "packing" process is described in greater detail below. The filler assembly (100), in the embodiment shown, includes a column coupling clamp (46) and a clamp (22). As shown, clamp (22) of FIGS. 1, 2 has been removed from tube (34), and its flange (FIG. 3) is coupled to a filler tube (44) by means of a column coupling clamp (46). The coupling clamp (46) operates to capture the chromatography tube (34) by utilizing an axial clamp seal (38) which closes around the flange (30) (FIG. 3) of chromatography tube 34 and is held closed by a fastener such as a clasp (24). The filler tube (44) may be captured, as in this embodiment, by using a screw cap (36). The screw cap (36) in this embodiment has an outer diameter larger than the flanged end of the filler tube (44). A person skilled in the art will recognize that the use of a flexible broken washer, elastomeric o-ring or other comparable device will improve the seal at the connection point between the flanged end of the filler tube and the screw cap (36). When the screw cap seal (36) is screwed into the column coupling clamp (46), which is threaded on the interior surface opposite the axial clamp seal (38), the filler tube (44) is captured and held in fluid communication with the chromatography tube (34). As with the column (10) in FIG. 2, in this embodiment a clamp (22) may be used to capture the end of the filler tube (44) opposite the column coupling clamp (46) and hold it in fluid communication with a piston tube (20).

Figure 5:
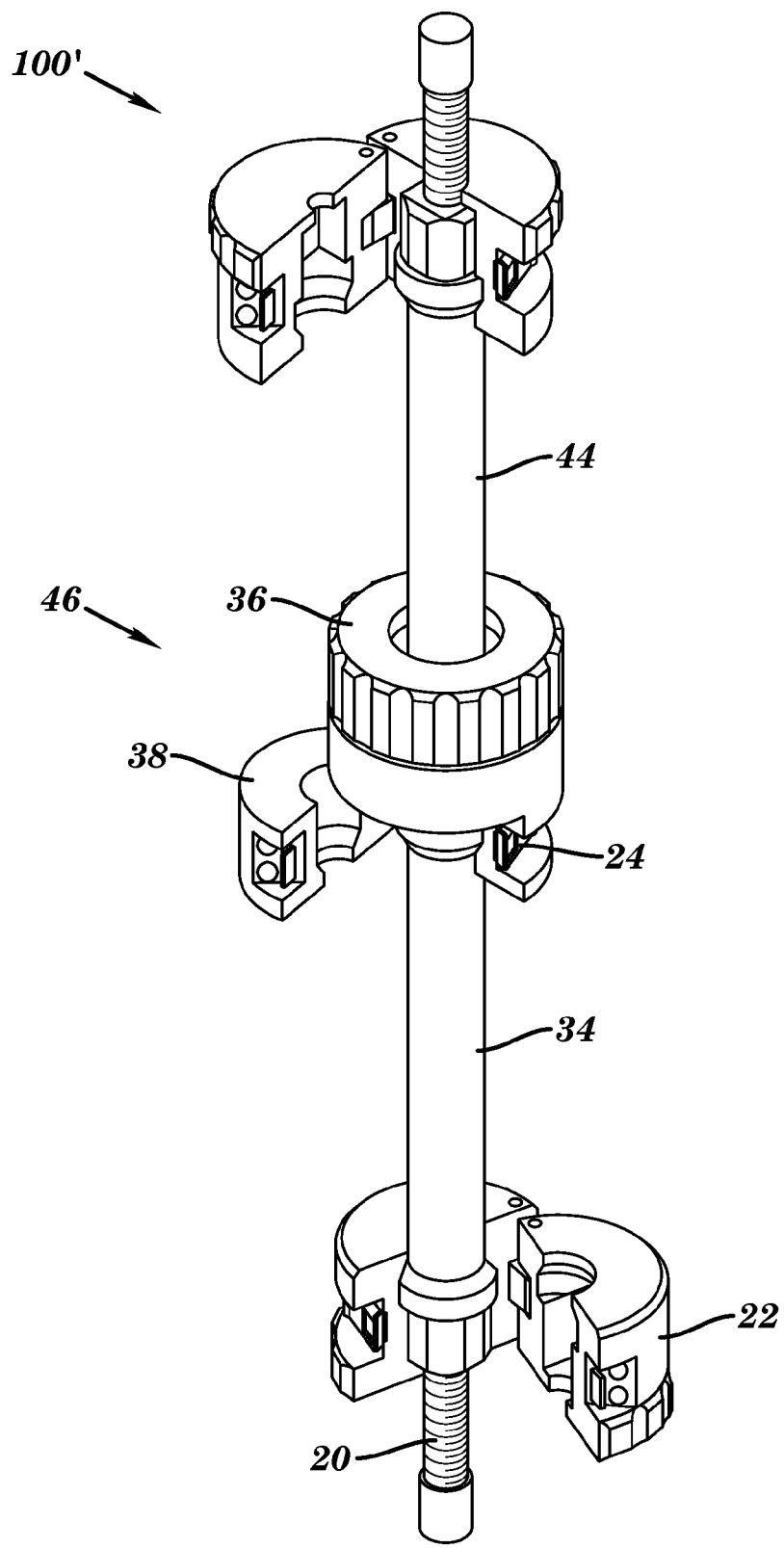
FIG. 5 is a perspective view of another alternate embodiment of the subject invention.

Referring to FIG. 5, in another embodiment, a tube assembly (100') is substantially similar to the tube assembly 100 with a second clamp (22) attached to the end of the chromatography tube opposite the end captured by the column coupling clamp (46). This clamp captures the end of the chromatography tube (34) and a second piston tube (20) and holds them in fluid communication with each other.

Substantially any material with the necessary physical properties required for conventional chromatography operations may be used for the components. Without restricting the possible materials that could be employed the applicant submits the following examples of exemplary materials that may be used to manufacture various components: Borosilicate glass for the chromatography and filler tubes (34,44); Teflon®, Polypropylene or Peek for the piston tube (20); Polyethylene, Stainless Steel, Porous glass or Titanium for the porous obstruction (48); Delrinn® for the clamp (22) and coupling clamp (46); Delrin® or Teflon® for the nut block, and Stainless steel for the clasp (24).

Note that the embodiments above are meant to illustrate various possible configurations of the present invention and the applicant does not restrict the application to these particular embodiments. As shown and described with respect to FIG. 2, one possible modification to any of the aforementioned embodiments and others would be to substantially permanently (or immovably) dispose a porous obstruction (48) at one end of the chromatography tube (34). Such a modification may eliminate the need for a clamp (22) at that end of the tube (34), thereby reducing the number of clamps (22) needed to assemble the column.

Figure 6:
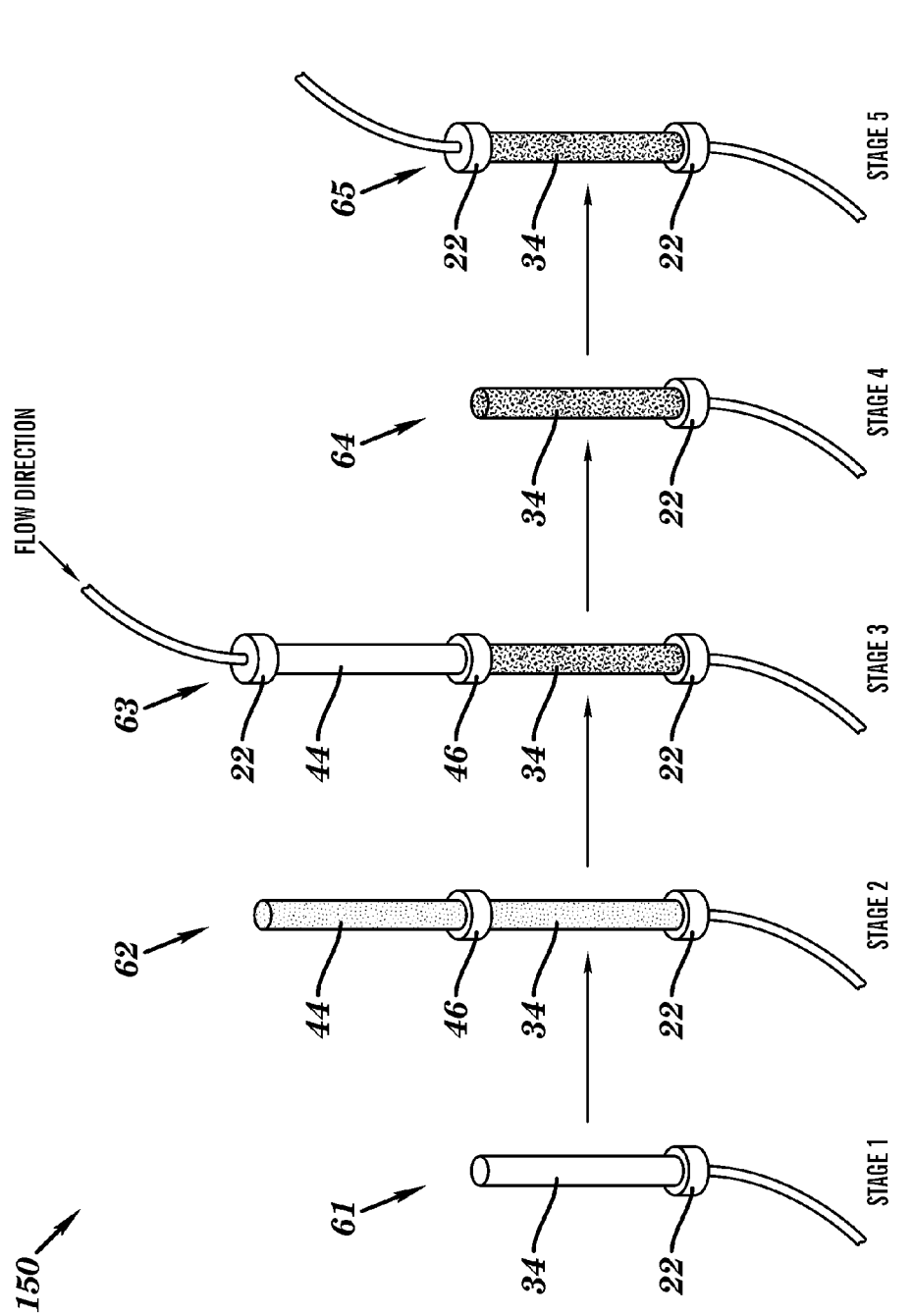
FIG. 6 is a flowchart showing a method of packing a chromatography column using an embodiment of the subject invention.

Referring to FIG. 6, a method (150) of packing a chromatography column (10') with stationary phase material using filler assembly (100') is shown and described. As mentioned hereinabove, prior to using a new or empty column (10') it is typically packed with stationary phase particles. Such stationary phase particles are well known to those skilled in the art, the most common being silica. A commercial example of a column-packing material used in newer systems would include GE Healthcare (Pharmacia) Superdex 75 (GE Healthcare, Piscataway N.J.). The stationary phase is typically purchased from a manufacturer in a range of particle sizes (e.g. a 10 micron media has a particle distribution of 7-12 microns).

In a first stage (61) a single chromatography tube (34) is connected by a clamp (22) to the downstream direction of a chromatography system. In the second stage a chromatography tube (34) coupled to a filler tube (44) using a coupling clamp (46). In the second stage (62), the column is filled with a slurry composed of a chromatography process fluid (mobile phase) mixed with a solid particle stationary phase and represented in the figure by hatched lines. For proper separation to occur in a chromatography process, it has been found that the particles are desirably packed with substantially even size distribution. One approach commonly used to help achieve such a distribution is slurry/flow packing. The slurry may be produced by mixing roughly equal parts of mobile phase and stationary phase outside the column in a container (beaker). The mix is typically 1:1 ratio, in essence doubling the volume of the finished stationary phase volume. This is the motivation for the column extension in this step (62) produced by the coupling of the chromatography (34) and filler tube (44). There is a porous obstruction at the bottom end of the vertical assembly that obstructs the passage of the particulate stationary phase from the chromatography tube (34) in the downstream direction.

In the third stage (63), a clamp (22) is closed around the open end of the filler tube (44) coupling the filler tube to a piston tube (20) and holding the column in fluid communication with the upstream portion of the chromatography system. Fluid is then pumped through the assembly under pressure.

This flow causes the stationary phase to settle, or pack, at the downstream end of the column with good particle distribution.

In the fourth stage (64), the upper part of the column assembly (parts 22, 44, and 46) are removed leaving a fully packed chromatography tube (34).

In the fifth stage (65), the top clamp (22) of stage 3 is attached to the top of the packed chromatography column (34). The piston (20) (reference FIG. 3) is lowered carefully, by rotating the clamp (22) relative to the tube (34) until the end of the piston (20) which contains a porous obstruction (such that the stationary phase particles cannot pass through it) contacts the top of the settled bed. The column is now ready to run chromatography (reference FIG. 1).

Note that this is one method for packing a chromatography column and that by describing it the applicant does not restrict the application to this one embodiment of a method of packing a chromatography column. Alternatively the packing may be accomplished without extending the column. The consequence of using the method of FIG. 6 without an extension is that whatever volume is occupied by the mobile phase in the slurry mixture will not be available volume for packing the stationary phase. It would also be possible to pack and begin the chromatography process described in FIG. 6 without performing the last two steps (64,65) but it is desirable that the packed stationary phase be held in place in a way comparable to that described above at the end of stage five (65) in FIG. 6

Having thus described the invention, what is claimed is:

1. A chromatography column, having a longitudinal axis, for use in a liquid chromatography process, said column comprising:
   a chromatography tube with an opening at both ends;
   a piston tube with an opening at both ends and an outer diameter smaller than an inner diameter of said chromatography tube;
   said piston tube having at least one porous layer obstructing a transverse cross section of its interior;
   at least one chromatography clamp;
   said chromatography clamp being selectively movable between open and closed positions, and configured to extend substantially 360 degrees about the periphery of said chromatography tube when closed, with no single component of said chromatography clamp extending substantially 360 degrees of said chromatography tube;
   said chromatography clamp configured to releasably maintain said chromatography tube and piston tube in fluid communication with one another;
   an interior surface of said chromatography clamp being threaded, sized and shaped to threadably engage an outer surface of said piston tube;
   said chromatography clamp configured to rotate relative to a periphery of said chromatography tube, while said piston tube is held rotationally static relative to said chromatography tube, wherein rotation of said chromatography clamp is configured to move said piston tube axially within said chromatography tube.

2. The column of claim 1 wherein at least one end of said chromatography tube is flanged.

3. The column of claim 1 wherein said piston tube is held rotationally static relative to said chromatography tube by an o-ring disposed in a substantially fluid-tight fit between said piston tube and said chromatography tube.

4. The column of claim 1, comprising:
   a collar configured to capture said piston tube and be captured by said chromatography clamp;
   an interior surface of said collar being threaded, sized and shaped to threadably engage said piston tube.

5. The collar of claim 4 wherein:
   said interior surface of said collar is threaded, sized and shaped to threadably engage said piston tube;
   said collar is configured to capture said piston tube by rotating said collar so that the interior threads of said collar cooperatively engage the exterior threads of said piston tube.

6. The column of claim 5 comprising a flange disposed at an end of said chromatography tube, and said chromatography clamp is configured to capture said flange and said collar to maintain said chromatography tube and piston tube in axial alignment with one another.

7. The column of claim 6 wherein said collar is held static relative to said chromatography clamp when said clamp is in the closed position.

8. The column of claim 1 wherein said chromatography clamp opens and closes by means of pivoting on a hinge mounted on said clamp.

9. The column of claim 1 wherein said chromatography clamp includes a releasable fastener mounted along the plane on which the chromatography clamp opens to releasably maintain chromatography clamp in closed position.

10. The column of claim 1, comprising porous obstruction substantially permanently disposed at one end of said chromatography tube, said porous obstruction extending across a transverse cross-section of the interior of said tube.

11. The column of claim 1 further comprising:
   a filler tube with an opening at both ends;
   a column coupling clamp;
   said column coupling clamp configured to capture said chromatography tube and said filler tube and releasably maintain said chromatography and filler tubes in fluid communication with one another.

12. The column of claim 11 wherein at least one end of said filler tube is flanged.

13. The column of claim 11 wherein said column coupling clamp is configured to be closed along a direction substantially transverse to said longitudinal axis to capture said chromatography tube;
   said column coupling clamp configured to be closed along a substantially axial direction to capture said filler tube.

14. A chromatography column, having a longitudinal axis, for use in a liquid chromatography process configured to connect to said process and convey eluent through the column and through the adsorbent contained in said column, said column comprising:
   a chromatography tube with an opening at both ends;
   at least one of said openings being flanged;
   a piston tube with an opening at both ends and an outer diameter smaller than the inner diameter of said chromatography tube
   the outer surface of said piston tube being threaded;
   said piston tube having at least one porous layer obstructing a transverse cross section of the interior;
   a collar for said piston tube;
   the interior surface of said collar being threaded sized and shaped to threadably engage said piston tube;
   said collar configured to capture said piston tube by rotating relative to said piston tube so that the exterior threads of said piston tube are captured by the interior threads of said collar;
   at least one chromatography clamp;
   said chromatography clamp configured to open along a substantially axial plane;
   said chromatography clamp configured to capture said flange and said collar and hold said chromatography tube and piston tube in axial alignment;

wherein said chromatography clamp is free to rotate relative to said flange;
wherein said chromatography clamp is held static relative to said collar;
wherein said piston tube is rotationally held static relative to said chromatography tube.

* * * * *